United States Patent [19]

Montalbano et al.

[11] Patent Number: 5,773,296
[45] Date of Patent: Jun. 30, 1998

[54] BEAD DISPENSER AND BEAD DISPENSER SYSTEM FOR IMMUNOASSAY ANALYSIS

[75] Inventors: Anthony P. Montalbano, Shelter Island Heights; Chris P. Montalbano; Greg A. Montalbano, both of Great Neck; Eric C. Fleischer, Rockville Centre, all of N.Y.

[73] Assignee: DPC Cirrus, Inc., Randolph, N.J.

[21] Appl. No.: 670,995

[22] Filed: Jun. 28, 1996

[51] Int. Cl.[6] .............................. G65N 37/00; B65H 3/60
[52] U.S. Cl. .............................. 436/43; 422/63; 422/64; 422/103; 422/104; 436/807; 221/264; 221/276
[58] Field of Search .............................. 422/63, 64, 68.1, 422/103, 104; 436/43, 47, 807; 221/264, 276, 202, 203

[56] References Cited

U.S. PATENT DOCUMENTS

| | | | |
|---|---|---|---|
| 4,101,284 | 7/1978 | Difiglio et al. | 23/259 |
| 4,405,060 | 9/1983 | Hsei | 221/135 |
| 4,415,098 | 11/1983 | Haas | 221/202 |
| 4,492,316 | 1/1985 | Emms | 221/202 |
| 4,937,048 | 6/1990 | Sakai et al. | 422/63 |
| 5,316,726 | 5/1994 | Babson et al. | 422/65 |

OTHER PUBLICATIONS

Trade Brochure, entitled "PK310 Fully Automated Enzyme Analyser", a publication of Olympus Biomedical Products Div., Wendenstrasse 14–16, 2 Hamburg 1, Germany, 15 pages, undated.

*Primary Examiner*—Long V. Le
*Attorney, Agent, or Firm*—Whitham, Curtis & Whitham

[57] ABSTRACT

A bead dispenser device, and a system comprising a plurality of same, useful for supplying, one at a time, beads for heterogenous immunoassay, including a track capable of storing and feeding a plurality of substantially spherical beads by effect of gravity to a lower track end, where the track is sealingly housed within an enclosure having a base including upper and lower sections defining a plunger chamber, and a bead chamber defined in the upper section communicating with the lower track end and the bead chamber being offset along the plunger chamber relative to a bead exit opening in the lower section, with a plunger sealingly provided in the plunger chamber capable of horizontal reciprocal movement within the plunger chamber, the plunger having a throughhole defining another bead chamber normally aligned with the first-mentioned bead chamber at the lower track end and with a plunger portion concurrently blocking the exit opening via a horizontal biasing device acting on the plunger, wherein when opposing horizontal force is exerted adequate to overcome the normal bias force the plunger moves horizontally to align the other bead chamber with the exit opening and allow a bead to be dispensed.

25 Claims, 2 Drawing Sheets

5,773,296

BEAD DISPENSER AND BEAD DISPENSER SYSTEM FOR IMMUNOASSAY ANALYSIS

BACKGROUND OF THE INVENTION

1. Field of the Invention

The invention is generally relates to a bead dispenser, and a bead dispenser system particularly well-suited for dispensing beads for use in an automated immunoassay analyzer.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other analyte compounds found in a test sample. For many years, immunoassays were performed by hand by trained laboratory technicians.

Recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody, the sample is incubated such that the corresponding antigen or antibody in the sample and a labeled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician, or monitored and displayed in real time as described in U.S. Pat. No. 5,316,726.

One conventional method for introducing a solid support bearing the appropriate antibody or antigen for the desired test on the analyte is by dropping a solid support in bead form into a test tube, and then the sample and reagents are added and the desired analysis conducted. For example, a trade brochure published by Olympus (Biomedical Products Division), Wendenstrasse 14-16, 2 Hamburg 1, Germany, describes a bead storage unit comprising a plurality of bead packs mounted on a carousel. Each bead pack stores a plurality of solid support beads as a column on a spiral track, where the beads exit the bottom of the spiral track into an open-air holding receptacle adjoining the outside of the base of the bead pack. The dispensed beads are picked up by a vacuum-operated bead transport for feeding into a U-shaped reaction tube.

Another conventional bead pack marketed by Roche Laboratories includes a spiral track for storing solid support beads with beads dispensed at a centrally-located exit hole and a three-pronged mechanical pick-up device is used to grasp and transport the dispensed bead to a reaction tube.

A bead dispenser device available from Abbott Laboratories is a manual operated dispenser with a plunger housed in a chamber in a non-hermetic manner. The chamber has a lower exit opening that is horizontally misaligned relative to an upper feed hole into the chamber. The plunger has a receptacle hole for receiving a bead that is aligned with the upper feed hole in the normal nonactuated position of the plunger. Manual actuation of the plunger horizontally displaces the plunger within the chamber such that a bead carried in the plunger receptacle hole is carried to and over the lower exit opening in the chamber whereby the bead can drop out of the dispenser device.

There remains a need for bead dispenser device, such as for use in immunoanalysis, that can store and dispense beads in a more hermetically-sealed manner.

SUMMARY OF THE INVENTION

It is an object of this invention to provide a bead dispenser capable of storing and serially dispensing biomaterial-coated support beads in a hermetically-sealed manner.

It is another object of the invention to provide a system of bead dispensers, each dispenser supplying a single type of biomaterial-coated bead and different dispensers supplying different types of biomaterial-coated beads relative to each other, such that an appropriate type of biomaterial-coated bead can be selected and dispensed.

It is a further object of the invention to use the aforesaid bead dispenser system on board an automated immunoassay analyzer to permit selective dispensing from among different types of biomaterial-coated beads with each type of bead associated with its own bead dispenser.

According to the invention, a unique bead dispenser device is utilized to directly dispense a biomaterial coated bead into a reaction tube with the biomaterial coated bead preserved in a hermetically-sealed environment up until it is actually dispensed into a reaction tube. To accomplish this objective, the bead dispenser device of the present invention has a bead storage unit having a track that stores and serially feeds beads directly into a base defining a plunger chamber. A plunger is provided within the plunger chamber that is capable of horizontal reciprocal movement within the chamber. A return spring is used to impose a normal bias on the plunger such that it has a position, at rest, within the chamber where a throughhole in the plunger aligns with the bead drop off point of the track in the bead storage unit. However, when the plunger is displaced by an external horizontal force in opposition to and greater than the bias imposed by the return spring, the plunger can be displaced within the chamber whereby the throughhole in the plunger can align with a bead exit opening in the base. A bead carried in the throughhole of the plunger drops out of the dispenser as the throughhole aligns with the exit opening. Once the external force is removed, the return spring pushes the plunger back into its original at rest position. The plunger itself is fitted with O-rings adequate to hermetically seal the interior of the storage unit from the ambient environment. That is, to ensure that the bead storage chamber is hermetically sealed at all times except during dispensing of beads from the plunger chamber, O-rings are sealingly fitted onto the neck portions at opposite distal ends of the plunger which form an air-tight seal with flanges on the inner wall of the plunger chamber. That is, an air and moisture seal is formed between the interior of the bead storage unit and the surrounding environment by an O-ring(s) fitted on each distal end of the plunger.

Once a bead is dispensed into a reaction tube by the bead dispenser of the invention, a sample of the analyte of interest and an appropriate reagent can be added thereto, and quantitation performed.

In another aspect of the invention, a plurality of the bead dispensers can be arrayed together with different bead dispensers storing different types of beads relative to each other. This arrangement allows for selective picking and matching of a desired type of bead as selected from among the varieties offered by the different bead dispensers for introduction into a reaction tube that is destined and predetermined to hold a particular sample analyte of interest for analysis.

Therefore, the present invention eliminates the need to preselect and make available an adequate number and types of assay tubes before commencing an immunoassay analysis, and it also avoids the concomitant additional handling and identifying requirements associated with conventional assay tube usage. In the present invention, the needed biomaterial-coated bead itself can be delivered directly to the reaction tube on board an immunoassay analyzer in a facile manner without the need for bulk handling and tracking of a carrier vessel for each bead as inventory up until its usage.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

The bead dispenser device and bead dispenser device system of the present invention can be a subsystem of an analytical instrument intended to produce reportable assay results through the processing of specimens and various other components of the chemistry system. This processing involves the control and timing of various internal operations as well as the acquisition and processing of data generated internally or through interaction with an external computer system such as LIS. The analytic instrument is an integrated electromechanical apparatus which processes specimens in order to generate test results. It is comprised of all the mechanical hardware, electronic hardware and software required to perform immunoassays described herein.

The analytical elements are biomaterial coated beads (e.g., about 0.25 inch diameters) used as the solid phase for heterogenous immunoassays to quantitate analytes in solution. One bead is consumed for each test conducted, and a particular type of bead can be used for any number of different assay types, depending on the reagent used therewith.

These beads are dispensed by the dispenser device, also referred to herein interchangeably as a "bead pack", into reaction tubes at a rate of one bead per tube. Beads are contained within disposable bead dispensers, each dispenser holding one type of bead. A plurality of dispenser devices can simultaneously reside in the system, e.g., as situated upon and traveling on a common carousel, and the operator can supplement or replace the supply of dispensers or packs at any time.

Figure 1A:
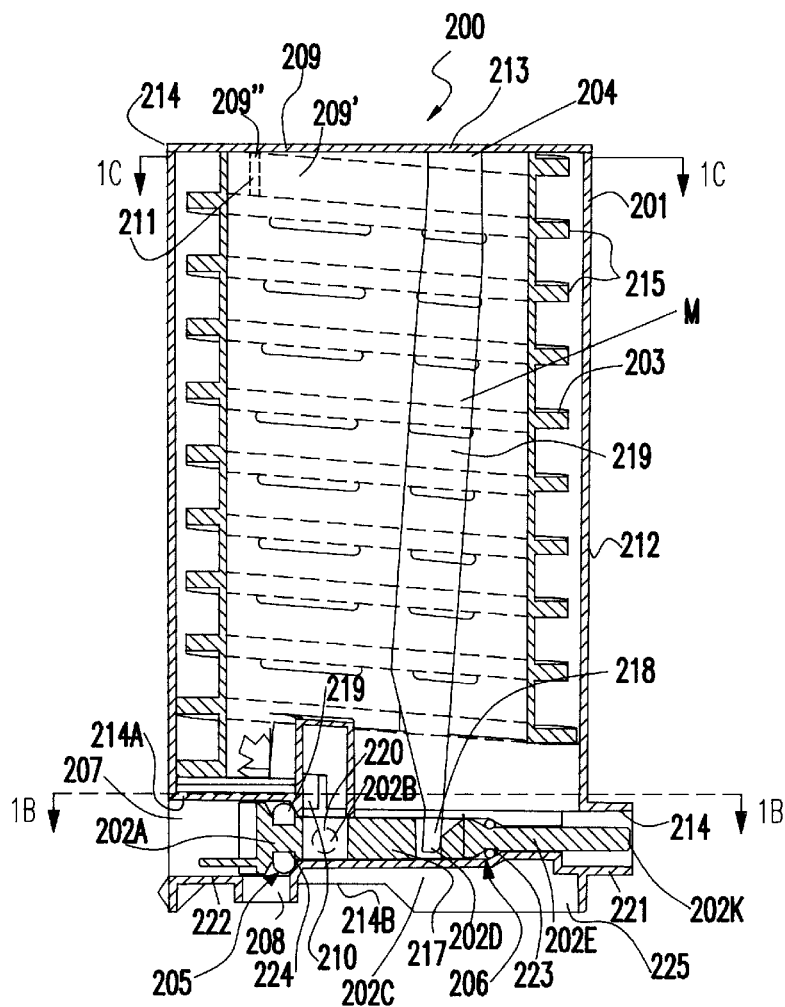
FIG. 1A is a cross-sectional side view of a dispenser device of the invention.

Referring now to the drawings, and more particularly to FIG. 1A, there is shown a bead dispenser device 200 of the invention useful for supplying, one at a time, beads for heterogenous immunoassay. The dispenser has a track 203, formed as a coiled-ramp-like structure, capable of storing and feeding a plurality of substantially spherical beads (not shown) by effect of gravity to a lower track end 210.

The track 203 serves as a bead support surface and has lateral outer side edges 215 which face sidewall 212 of the chamber 215 in closer proximity than the bead diameter, such as seen in the fragmentary view of FIG. 1A, such that the inner surface of chamber sidewall 212 delimits lateral movement of a bead on the smooth supporting or lower surface 216 of the track 203. The bead support surface 216 extends continuously between an upper track end 209 and the lower track end 210. The track 203 includes a plurality of turns between the upper track end 209 and the lower track end 210. The provision of turns serves to effectively lengthen the distance between the upper track end 209 and the lower track end 210, so that more beads effectively can be stored and supplied along the track 203. The turns must have enough height clearance provided between successive turns to avoid frictional contact with the top of the beads. Also, the track 203 must have enough grade or inclination (angle α in FIG. 2) provided relative to the horizontal direction (y-direction) to allow the force of gravity to act on the beads to overcome any frictional forces to cause the descent of the column of beads down the track 203 to the lower track end 210.

Figure 2:
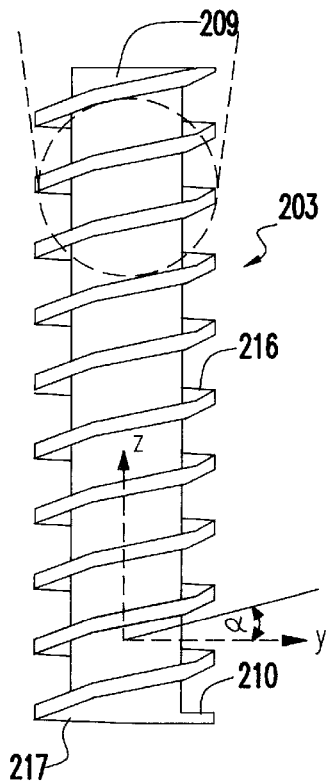
FIG. 2 is a fragmentary side perspective view of the bead track component of the dispenser device of FIG. 1A.

In a preferred embodiment, the track 203 traces an oval-shaped, spiral path extending from the upper track end 209 to the lower track end 210 winding around a common longitudinal axis (Z-axis in FIG. 2). The spiral path of the track can also trace a helical path, although an oval shape is preferred as it maximizes track space on an arcuate segment. The spiral path preferably has a constant periodicity between the upper track end 209 and the lower track end 210, although this is not essential, as it is only necessary to ensure adequate height clearance is provided for the beads between successive turns of the spiral path. The track 203 is inclined at an angle a preferably between about 2° to about 6°, and more preferably about 4°, relative to the horizontal direction (y-axis). The selection angle a is a tradeoff between providing enough clearance for the beads between successive turns of the track 210 and ensuring a steep enough grade for rollability of the beads down the track 210. In one embodiment, seen in FIGS. 1C and 1A, the uppermost rung of the track 203 has an integral cover 203t having an opening 209' and a backstop 209" to permit top loading of beads. The oval-shape of the track can have about a 15° convergence angle γ (FIG. 1C) towards its smaller radius end. A central opening "c" is left inside the track 203 for attaching the spring finger and for any desired storage of dessicant. The track 203 preferably is formed of molded plastic to provide the structural features disclosed herein in an integral structure.

Returning more specifically to FIG. 1A, an enclosure or chamber 201 hermetically seals and houses the track 203 and comprises a side wall 212 enclosing outer lateral surfaces 215 of the track 203, a cover 213, such as a rigid thermoplastic lid member that is ultrasonically welded to the upper end 214 of the chamber side wall 212 after insertion of the integral track piece 203 within the chamber 201 and loading the beads on the track. The cover 213 hermetically seals the top end of the chamber 201. Side wall 212 can be a continuous oval-shaped or cylindrical shell, such as constituted by thermoplastic material. The chamber 201 also includes a base 214 including upper section 214a and a lower section 214b, which together define a plunger chamber 207. The chamber 201 preferably contains a dessicant material (not shown), such as located within a central open area encircled by the spiral track 203.

Figure 1B:
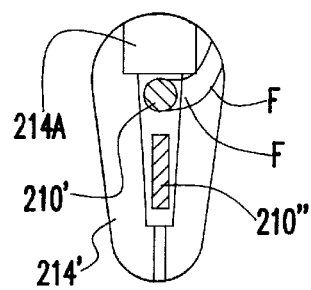
FIG. 1B is a cross-sectional top view of the bead chamber and its plunger chamber from the perspective of direction 1B—1B indicated in FIG. 1A.

A first bead chamber 217 is defined by the upper section 214a of chamber base 214 communicating with the lower track end 210 and the first bead chamber 217 being offset along the plunger chamber 207 relative to a bead exit opening 208 in the lower base section 214b. The base 214 has a mounting flange 225 projecting around the periphery of the bottom of the chamber 200. As best seen in FIG. 1B, opening 210', having a diameter slightly larger than the bead diameters, is provided through upper base section 214a where opening 210' aligns with track end 210 when the spiral track 203 is inserted into chamber 201. The upraised portion of fins "f" project upward from base section 214a to define first bead chamber 217 providing a short bead directing channel between the track end 203 and the opening 210' through upper base section 214a. An opening 210" is formed upper base section 214a adequate to permit insertion and movement of spring finger 218 towards and away from opening 210'. Upper base section 214a is upraised from medial plastic 214' joining the plunger chamber 207 to the chamber sidewall 212. Downward projecting lower base section 214b and upper base section 214 meet at medial flat plastic 214' to define the plunger chamber 207 compartment.

Figure 4:
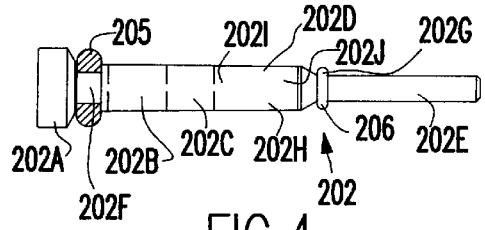
FIG. 4 is a fragmentary side perspective view of the plunger component of the dispenser device of FIG. 1A.

A plunger 202 is inserted into plunger chamber 207 and is capable of horizontal, reciprocal movement within the plunger chamber 207. As better seen in the side fragmentary view of FIG. 4, plunger 202 is a rigid material, such as metal, wood, composite, or hard plastic, with, one end, a head 202a and collar portion 202f capable of horizontal movement within the larger recess 222 in chamber base 214, with movement delimited rightward, as seen in FIG. 1A, by flange 219 in the inner wall of plunger chamber 207 of chamber base 214. On the opposite end of plunger 202 there is a distal neck 202e sized to enter flange 223 of base section 214 and to slidably conform to the smaller recess 221 defined in chamber base section 214. The distal neck 202e adjoins shoulder portion 202h via collar portion 202g. The collar portions 202f and 202g have O-rings 205, 206, respectively, fitted thereon. Collar portion 202f, as with medial section 202c, is rectangular in cross section. Therefore, for the embodiment illustrated, the O-ring 205 fitted on collar 202f assumes a substantially rectangular profile when mounted. The O-ring 206 is circular in profile when mounted on collar 202g.

In the medial section 202c of the plunger, a recess 202d is provided to engage a fingered (free) terminal end 218 of a spring 219, described in greater detail elsewhere herein. The medial section 202c of plunger 202 also has throughhole 202b that is sized large enough to permit unrestricted movement of a single bead 220 (shown in phantom lines in FIG. 1A) to enter, temporarily reside within, and egress the throughhole 202b. As can be understood from an objective of the invention of providing biomaterial coated beads to reaction tubes, it is important that the throughhole 202b have size adequate to accommodate a single bead, but no more, so that each reaction tube receives one and only one bead when ejected from the dispenser device.

The plunger 202 is depicted in its at rest mode, i.e., non-actuated mode, in FIG. 1A, whereby bead exit opening 208 is closed or blocked by a solid portion of the plunger 202. That is, the plunger 202 has a through-hole 202b defining a second bead chamber 202b. This throughhole 202b is normally aligned with the first bead chamber 217 at the lower track end 210 and with a plunger portion 202a concurrently blocking the exit opening 208 via a biasing means.

Figure 3:
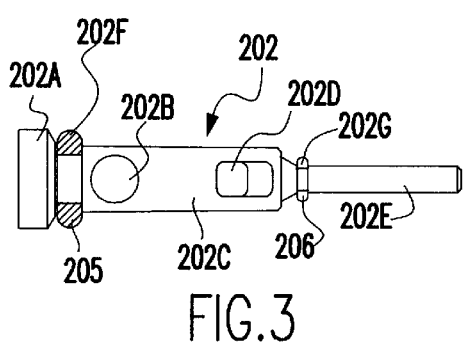
FIG. 3 is a fragmentary top perspective view of the plunger component of the dispenser device of FIG. 1A.
Figure 1C:
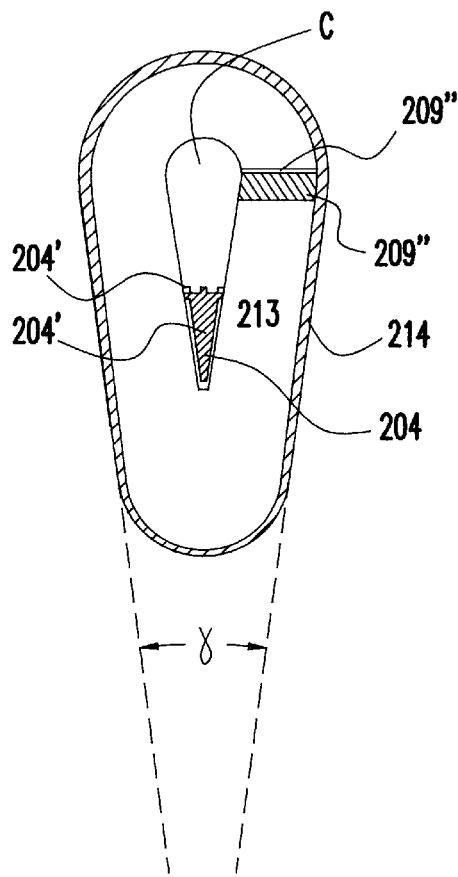
FIG. 1C is a cross-sectional top view of the bead chamber, bead track, and plunger biasing spring from the perspective of direction 1C—1C indicated in FIG. 1A.

The biasing means is depicted as a spring 219, such as a molded polypropylene plastic blade-like member, terminating at its lower end in a spring finger 218 that imposes a horizontal bias force on the plunger 202 (rightward in the perspective of FIG. 1A). FIG. 1A shows the side profile of the blade-like spring 219. The spring 219 has a medial portion "m" extending substantially perpendicularly through an opening in the enclosed central portion of the spiraled track 203 relative to the longitudinal axis of the plunger 202 from an upper end 204 attached physically to the track 203, down to the free end 218. The spring finger 218 normally biases the plunger 202 in the position seen in FIG. 1A with horizontal force acting upon the plunger in the direction rightward toward section 202e. The spring means 219 preferably is a discrete plastic elongated piece, such as made of molded polypropylene, which is rigid yet which will tend to flex or spring back to it original position if deflected at its unfixed end. As seen in FIG. 1C, the upper end 204 of spring 219 is mechanically snapped into flanges 204' formed on the inner periphery of central opening "c" inside track 203 in order to mechanically attach the top end 204 of spring 219 to the track 203. The spring 219 is effectively activated during the assembly of the track 203 and spring 219 with the integral chamber 201 and base 214 (housing the plunger 202) in the following manner. During assembly, the plunger 202 is inserted plunger chamber 217. The spring 219 is mechanically snapped into place at its upper end 204 to the track 203. Then, the track 203 and spring 219 are inserted within plunger chamber 207 until the finger latch 218 slides into the notch 202d in the plunger 202 and exerts a rightward pushing force on the plunger 202 (in the perspective of FIG. 1A) until the plunger shoulder 202h abuts flange 223 of plunger chamber 207 via intervening O-ring 206. As shown in FIGS. 1A and 3, the notch 202d has bevelling at it upper right end to facilitate entry of finger latch 218 into notch 202d.

In the use of the dispenser device of the invention, exit opening 208 of the dispenser device is positioned directly over a mouth of a reaction tube, then an external force (not shown) is applied to the outer end of section 202e of plunger 202 that is sufficient in magnitude to overcome the internal opposing biasing force of spring 204, so as to displace the plunger 202 leftward (in the view of FIG. 1A) a distance sufficient to align bead chamber 202b of the plunger with exit opening 208, at which point the bead contained and waiting in bead chamber 202b drops by the force of gravity out of the bead chamber, through exit opening 208, and into a reaction tube (or to intermediary means such as tubing used to transport the bead to a reaction tube).

After the bead drops from the plunger 202, the external force is withdrawn and the internal bias forces imposed by spring end 218 acting on abutting portion 202h of plunger 202 causes the plunger 202 to retract to its original position shown in FIG. 1A. Then, as the throughhole 202b re-aligns with the bead chamber 217 at the lower track end 210, the next bead that had been waiting in bead chamber 217 will drop by the force of gravity and by virtue of the weight of the column of beads there behind, into the now vacant throughhole 202b of plunger 202. As the successive bead drops into throughhole 202b, another bead successively moves down to bead chamber 217 at the track end 210 to take its predecessor's place, and so on, for each ejected bead, until the supply of beads is exhausted, the remaining beads deemed expired, or so forth.

To ensure that the chamber 201 is hermetically sealed, O-rings 205 and 206 each are insert molded onto the collar portions 202f and 202g, respectively, of plunger 202 which sealingly engage flanges 224 and 223, respectively, of the plunger chamber 207 of the base section 214. The flange 223 of plunger chamber 207 is inclined at an acute angle of approximately 60° from vertical. By contrast, flange 224 of plunger chamber 207 is inclined at a relatively sharper acute angle of approximately 30° from vertical. As a consequence, overtravel of the plunger 202 is permitted in that a "soft stop" is created at O-ring 206 on the more gentle slope presented by the surface flange 223. Again, the return of plunger 202 after completing a dispensing of a bead is brought about by the bias action of spring 219. In any event, the O-ring 206 contacts flange 223 before O-ring 205 contacts flange 223 by proper dimensioning of the components involved such that O-ring 206 can be squeezed during return of the plunger 202 after dispensing of a bead and removal of actuation force on plunger face 202k. This permits a variable degree of compression of O-ring 206 against the surface of flange 223 until O-ring 205 on the opposite end of the plunger 202 makes a "hard stop" with the steep surface of flange 224. This arrangement of flanges 223 and 224 with O-rings 206 and 205, respectively, prevents sliding friction from occuring between the plunger chamber 207 and the plunger 202.

To impose the normal bias on plunger 202 via spring 219, when plunger 202 is in the closed position depicted in FIG. 1A, the spring 219 is inclined leftward (in perspective of FIG. 1A) at an angle of approximately 3.5° from vertical. This angle is created during assembly of chamber 200 where spring 219 is mechanically attached to the track 203 at its upper end 204 while lower finger 218 is pushed downward such that it slips down inclined wall 202j of plunger notch 202h and ultimately into abutment with the right vertical wall 202i defining plunger notch 202d.

To dispense a bead, a horizontal force is exerted leftward on the right exposed face 202k of plunger distal neck 202e in opposition to and adequate to overcome the opposing normal bias force created in the inclined spring 219. As a result, the plunger 202 horizontally moves (leftward in the perspective of FIG. 1A) to ultimately align the second bead chamber 202b with the exit opening 208 at which point the bead held in plunger receptacle 202b drops out of the plunger 202 and exits the chamber 200 via exit opening 208.

Figure 5:
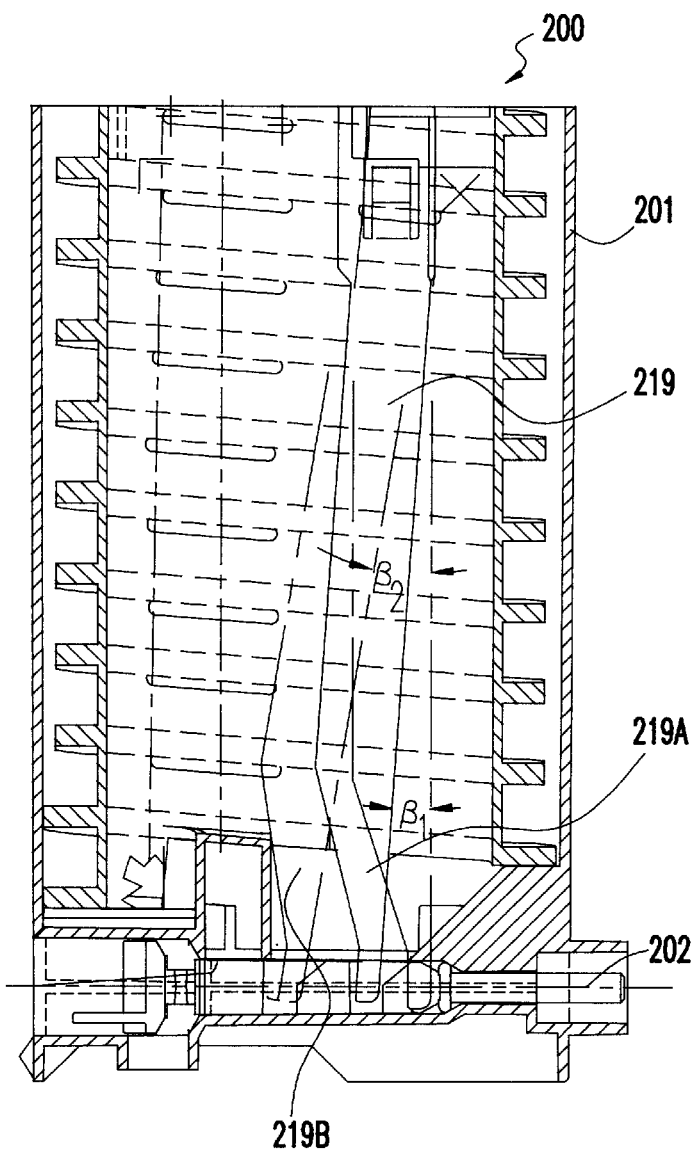
FIG. 5 is a cross-sectional side view of a dispenser device of the invention showing the at rest and dispensing modes of the device.

To show the range of movement of the spring 219 during such a dispensing operation, in FIG. 5, spring 219 has an initial angle $\beta_1$ of approximately 3.5° to the vertical in its at rest position 219a and as attached at its upper end 204 to track 203 before dispensing of a bead is initiated. When the plunger 202 is actuated to dispense a bead, the plunger 202 is deflected leftward (in the perspective of FIG. 5) a distance such that spring 219 becomes inclined at position 219b at an angle $\beta_2$ of approximately 9° to vertical at which point receptacle 202b is aligned with exit opening 208 and the bead can drop. Once the actuation force is relieved from right endface 202k of plunger 202, the flexure intrinsic to the plastic spring 219 will cause it to automatically return back to its initial angle $\beta_1$ of approximately 3.5° to the vertical as its at rest position 219a.

The bead dispenser of this invention thus can serve the following functions:

a) to protect the beads contained therein from environmentally induced damage;

b) to package the beads in a fashion convenient for operator access and handling;

c) to facilitate the dispensing of a single bead into each reaction tube as needed;

d) to provide the necessary space for identification and product labeling; and e) to enable visual estimation of bead inventory by the operator.

To provide the ability to perform a wide variety of different types of immunoassays on board a common immunoassay analyzer, the bead dispenser of this invention is effectively used, in another aspect of the invention, in combination with a plurality of like bead dispenser devices useful for supplying beads, one at a time, for heterogenous immunoassay to a common location for addition to reaction tubes. Each such dispenser device comprising the structure described herein and any given dispenser device being loaded with beads all having the same biomaterial coated thereupon, with the proviso that at least one or more of the bead dispensers stores a different type of biomaterial as coated on its beads as compared to its cohort dispenser devices.

A carousel system, such as rotatable platform, can be used to accommodate a large number of bead dispensers of the invention, e.g., up to about 24 or even more, each dispenser being capable of holding large numbers of beads. For instance, the bead dispensers of the present invention typically are loaded with about 200 beads. The entire carousel preferably is housed within a dehumidified chamber maintained at about 10% relative humidity.

The carousel platform holding the dispensing devices can be rotated 360° to allow any given dispenser device to be moved by an identifying and selecting means to a bead loading station where the carousel passes over and intersects (in a top view) the track of a reaction tube loading chain.

For this embodiment, it is useful and practical to provide means for identifying each of the plurality of dispenser devices, such as by a readable bar code associated with each dispenser device, and the system further comprising a selecting means, such as including a bar code reader, for identifying and selecting from among the plurality of dispenser devices. For example, vertically oriented bar codes can be applied to each bead dispenser making it accessible to reading by a dedicated CCD bar code reader. The system also includes means electromechanically activatable for displacing a plunger of a selected dispenser device as positioned at the bead loading station over a reaction tube to cause one bead to drop from said exit opening into the mouth of the reaction tube.

In conjunction therewith, there will also be means provided for identifying a reaction tube and its intended analyte contents and relating the reaction tube back to the related dispenser device having a given biomaterial bound to a surface of the beads. Such system can include a tube transport means capable of moving the identifiable reaction tube to a bead loading station, relating the identified reaction tube to a related dispenser device having a given biomaterial bound to a surface of the beads as needed to conduct the assay desired for the sample of interest subsequently to be added to the reaction tube. Once the related dispenser device and reaction tube are aligned at the bead loading station, then a bead is ejected from the related bead dispenser into the reaction tube, and then the reaction tube is conveyed with the bead out of the bead loading station to additional stations to conduct the immunoassay itself (e.g., sample and reagent addition, incubation, washing, quantitation, and so forth), and the next reaction tube is brought to the bead loading station, and the operation repeated for all reaction tubes to be analyzed.

While it is preferred to commonly arrange the bead dispensers on a rotatable carousel whereby bead exit openings of said bead dispensers are selectively movable over said reaction tube at the bead loading station, other suitable arrangements are contemplated as well.

As noted above, the bead dispensers are identifiable such as by being bar code labeled with all the information needed to identify them to both the instrument and the operator. For example, bead dispenser labels can include the following exemplary data fields in both machine and human readable formats:

a) test code
 b) lot number
 c) expiration date
 d) serial number
 e) initial number of beads in the dispenser.

A preferred usage of the bead loading system of this invention involves integrating it into an immunoanalyzer system which maintains an internal database of all bead dispensers which are currently operational, i.e., "active". An active bead dispenser is defined as a bead dispenser which meets the following criteria:

a) bead dispenser bar code has been read by the instrument;
 b) the bead dispenser has not expired;
 c) the bead dispenser has not been exhausted.

Each bead dispenser may contain only one type of bead. However, a given bead dispenser may be used for several different test types when used in combination with different reagent packs or compartments within reagent packs.

In one preferred mode of using the bead dispenser system of the invention in an immunoanalyzer, when the analyzer first encounters a bead dispenser of a particular test type and serial number, it will initialize an internal database to reflect the initial number of beads in that bead dispenser. Then, each time a bead is dispensed from the bead dispenser, this internal counter will be decremented. Whenever a new run is initiated, the instrument will verify that sufficient fresh (not expired) beads for each test are available on board. If not, operators will be advised to add another suitable bead dispenser before leaving the instrument unattended.

The following series of steps then can be executed to dispense a bead into a reaction tube to prepare same for subsequent analyte/reagent addition and analysis:

a) rotation of the bead carousel to position the selected bead dispenser over the tube load chain;
 b) ejection of a single bead into the reaction tube on the tube load chain;
 c) decrementing of the instruments' internally stored bead count for the bead dispenser being processed; and
 d) verification that only one bead was dispensed into the tube.

Regarding possible information input problems, when the bead carousel is accessed, the analyzer preferably should have support software to verify the availability of all required information. If any is lacking, e.g., the bar code is unreadable or there is an absence of information about which tests to run or how to run them, the operator will be alerted immediately. As such, the analyzer can be programmed to proceed to process all on-board specimens before requiring further attention. Regarding possible test specific problems, if no beads were dispensed, an additional attempt will be made to do so. If two beads were dispensed, the bead dispenser's bead count will be decremented by two, a new reaction tube drawn and an additional attempt made to dispense a bead. If the second attempt fails, operators are alerted immediately of the problem via both on-screen and audible alarms. Meanwhile, the analyzer can be programmed to continue to process other test types while waiting operator intervention. As to possible hardware problems, such as bead carousel component failures, jams, excessive humidity in the chamber, and so forth, operators are alerted immediately of such problems via both on-screen and audible alarms. Until the operator intervenes, sampling operations will be suspended, but the tube processor operations can programmed to continue.

The basic overall series of steps use to perform a immunoanalysis test on a sample of interest with use of the bead dispenser system of this invention, is as follows:

A) deposition of reaction tubes onto a reaction tube load chain;
 b) deposition of beads into reaction tubes using the inventive bead dispenser system;
 c) transfer reaction tubes from reaction tube load chain to a pipetting station for depositing the specimen (analyte of interest) and liquid reagent into the reaction tube (already containing the bead);
 d) incubation and agitation of reaction tubes;
 e) optional washing;
 f) optional (e.g., chemiluminescent) substrate addition, incubation, addition of trigger compounds;
 g) quantitation of analyte (e.g., by reaction tube light output measurement); and
 h) discharge of spent tubes.

An analyzer using the bead loading system and scheme of the present invention represents a high throughput automated immunoassay system capable of assaying a broad range of analytes in serum, plasma, and urine. It is also contemplated within the scope of the invention that specific chemistry kits might also handle clarified cerebrospinal fluid or saliva. The system imparts a high degree of automation to a diverse set of immunoassays, such as encountered in hospital and commercial laboratory settings. As such, high volume testing (up to even 200 tests results per hour) is expected and must be accommodated. In addition, the urgency of medical decisions that will depend on the results of these assays dictates a rapid analytical response time.

The biomaterial coated beads themselves comprise an inert substrate, such as plastic, having a surface, wherein a biomaterial is bound to said surface. The biomaterial generally is selected from an antigen or an antibody. For example, the invention will support the following test categories: thyroid function, sex hormones, growth hormones, tumor markers, infectious diseases, allergy testing, immunoglobin and related proteins and peptides, steroids and other small molecules, therapeutic drugs, drugs of abuse, and vitamins. The immunological chemistries can be processed in any of the following formats: competition assays, sandwich assays, and liquid phase capture assays.

While the invention has been described in terms of its preferred embodiments, those skilled in the art will recognize that the invention can be practiced with modification within the spirit and scope of the appended claims.

We claim:

1. Bead dispenser device useful for supplying, one at a time, beads for heterogenous immunoassay, comprising:
   (a) a track capable of storing and feeding a plurality of substantially spherical beads by effect of gravity to a lower track end,
   (b) an enclosure sealingly housing said track, comprising:
      a side wall enclosing outer lateral surfaces of said track,
      a cover sealingly enclosing an upper track end of said track and upper end of said side wall, and
      a base including upper and lower sections defining a plunger chamber, and a first bead chamber defined in said upper section communicating with said lower track end and said first bead chamber being offset along said plunger chamber relative to a bead exit opening in said lower section,
   (c) a plunger sealingly provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal horizontal bias force said plunger being capable of horizontal movement to align said second bead chamber with said exit opening, said normal biasing force of said biasing means capable of horizontally moving said plunger effective to reblock said exit opening upon removal of said opposing force, and wherein said plunger further comprises first and second resilient sealing rings spaced apart and seated on respective first and second collar portions of said plunger, and said plunger chamber having first and second flanges capable of sealingly engaging said first and second resilient sealing rings, respectively, where said first flange is located between said exit opening and said first bead chamber and said second flange is located between said biasing means and a distal end of said plunger at which said horizontal force is exerted.

2. The bead dispenser device of claim 1, wherein said plunger comprises a notch receiving a fingered free end of said horizontal biasing means, said horizontal biasing means having an upper end attached to said track and a medial portion extending substantially perpendicularly relative to a longitudinal axis of the plunger to terminate in said free end.

3. The bead dispenser device of claim 1, wherein during said blocking of said exit opening by said plunger portion, said first resilient sealing ring sealingly confronts said first flange of said plunger chamber inclined at an acute angle of approximately 60° from vertical, and said second resilient sealing ring sealingly confronts said second flange of said plunger chamber inclined at an acute angle of approximately 30° from vertical.

4. The bead dispenser device of claim 1, wherein said track comprises a bead support surface and lateral edges delimiting lateral movement of a bead on said support surface.

5. The bead dispenser device of claim 1, wherein said bead support surface extends continuously between an upper track end and said lower track end.

6. The bead dispenser device of claim 1, wherein said track includes a plurality of turns between said upper track end and said lower track end.

7. The bead dispenser device of claim 1, wherein said track traces an oval spiraled path extending from said upper track end to said lower track end winding around a common longitudinal axis.

8. The bead dispenser device of claim 6, wherein said spiral path has a constant periodicity between said upper track end and said lower track end.

9. The bead dispenser device of claim 1, wherein said track is inclined at an angle between about 2° to about 6° relative to a horizontal plane.

10. The bead dispenser device of claim 1, wherein said side wall comprises an oval shape.

11. The bead dispenser device of claim 1, further comprising a dessicant material located inside said enclosure.

12. The bead dispenser device of claim 1, further comprising a plurality of substantially spherical beads supported on said support surface of said track.

13. The bead dispenser device of claim 11, wherein said beads comprise an inert substrate having a surface, wherein a biomaterial is bound to said surface.

14. The bead dispenser device of claim 13, wherein said biomaterial is selected from an antigen or an antibody.

15. A bead dispenser system, comprising:
   (1) a plurality of bead dispenser devices useful for supplying to a common location, one at a time, beads for heterogenous immunoassay, each dispenser device comprising:
      (a) a track capable of storing and feeding a plurality of substantially spherical beads by effect of gravity to a lower track end,
      (b) an enclosure sealingly housing said track, comprising:
         a side wall enclosing outer lateral surfaces of said track,
         a cover sealingly enclosing an upper track end of said track and upper end of said side wall, and
         a base including upper and lower sections defining a plunger chamber, and a first bead chamber defined in said upper section communicating with said lower track end and said first bead chamber being offset along said plunger chamber relative to a bead exit opening in said lower section,
      (c) a plunger sealingly provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal horizontal bias force said plunger being capable of horizontal movement to align said second bead chamber with said exit opening, said normal horizontal biasing force of said biasing means capable of horizontally moving said plunger effective to reblock said exit opening upon removal of said opposing force, and wherein said plunger further comprises first and second resilient sealing rings spaced apart and seated on respective first and second collar portions of said plunger, and said plunger chamber having first and second flanges capable of sealingly engaging said first and second resilient sealing rings respectively, where said first flange is located between said exit opening and said first bead chamber and said second flange is located between said biasing means and a distal end of said plunger at which said horizontal force is exerted; and (2) means for identifying each of said dispenser devices.

16. The bead dispenser system of claim 15, wherein said means for identifying each of said plurality of dispenser devices includes a readable bar code associated with each said dispenser device, and said system further comprising a selecting means for identifying and selecting from among said plurality of dispenser devices including a bar code reader.

17. The bead dispenser system of claim 16, further comprising selecting means for identifying and selecting one of said plurality of dispenser devices, and means for displacing a plunger of said selected dispenser device effective to cause one bead to drop from said exit opening.

18. The bead dispenser system of claim 15, further comprising means for selecting a dispenser device among said plurality of dispenser devices including a dispenser device carousel with an associated bar code reader.

19. The bead dispenser system of claim 15, further comprising a plurality of substantially spherical beads supported on said support surface of each said track of each said dispenser device, wherein said beads comprise an inert substrate having a surface, wherein a biomaterial is bound to said surface.

20. The bead dispenser system of claim 19, wherein, for each dispenser device, said biomaterial comprises the same material for all beads contained by said dispenser device, and said system further including a first dispenser device containing beads with a first type of biomaterials and a second dispenser device containing beads with a second type of biomaterial, where said first type of biomaterial is different from said second type of biomaterial.

21. A method for dispensing beads for heterogenous immunoassays, comprising the steps of:

(a) providing a bead dispenser system, including:
  (1) a plurality of bead dispenser devices arranged to supply to a common location, one at a time, beads for heterogenous immunoassay, each dispenser device comprising:
    (i) a track storing and feeding a plurality of substantially spherical beads by effect of gravity to a lower track end, said beads for a given dispenser device comprising the same biomaterial bound to a surface of said beads,
    (ii) an enclosure sealingly housing said track, comprising:
      a side wall enclosing outer lateral surfaces of said track,
      a cover sealingly enclosing an upper track end of said track and upper end of said side wall, and
      a base including upper and lower sections defining a plunger chamber, and a first bead chamber defined in said upper section communicating with said lower track end and said first bead chamber being offset along said plunger chamber relative to a bead exit opening in said lower section,
    (iii) a plunger sealingly provided in said plunger chamber and being capable of horizontal reciprocal movement within said plunger chamber, said plunger having a through hole defining a second bead chamber normally aligned with said first bead chamber at said lower track end and with a plunger portion concurrently blocking said exit opening via a horizontal biasing means imposing a bias force on said plunger, wherein when a horizontal force is exerted in opposition to and adequate to overcome said normal bias force said plunger being capable of horizontal movement to align said second bead chamber with said exit opening, and wherein said plunger further comprises first and second resilient sealing rings spaced apart and seated on respective first and second collar portions of said plunger, and said plunger chamber having first and second flanges capable of sealingly engaging said first and second resilient sealing rings, respectively, where said first flange is located between said exit opening and said first bead chamber and said second flange is located between said biasing means and a distal end of said plunger at which said horizontal force is exerted;
  (2) means for identifying each of said dispenser devices;
(b) providing at least one reaction tube;
(c) providing means for identifying said at least one reaction tube and relating said reaction tube to a related dispenser device having a given biomaterial bound to a surface of the beads;
(d) providing a tube transport means capable of moving said reaction tube to a bead loading station;
(e) moving said reaction tube to said bead loading station;
(f) ejecting a bead from said related bead dispenser into said reaction tube;
(g) adding a sample of an analyte of interest and a reagent into said reaction tube;
(h) quantitating the amount of analyte of interest; and
(g) repeating steps (c)–(h) for each additional reaction tube.

22. The method of claim 21, wherein said bead dispensers are commonly arranged on a rotatable carousel whereby bead exit openings of said bead dispensers are selectively movable over said reaction tube at said bead loading station.

23. The bead dispenser device of claim 1, wherein said first collar is a rectangular-shaped recess in said plunger and said first resilient ring comprises a rectangular-shaped O-ring, and said second collar is circular-shaped recess in said plunger and said second resilient ring comprises a circular-shaped O-ring.

24. The bead dispenser device of claim 1, wherein during said blocking of said exit opening by said plunger portion, said first resilient sealing ring sealingly confronts said first flange of said plunger chamber inclined at a first acute inclination angle from vertical, and said second resilient sealing ring sealingly confronts said second flange of said plunger chamber inclined at a second acute inclination angle from vertical, wherein said second inclination angle is smaller in inclination than said first inclination angle an amount effective to permit said second resilient sealing ring to variably compress until said first resilient sealing ring stops on said first flange.

25. Bead dispenser device useful for supplying, one at a time, beads for heterogenous immunoassay, comprising:

(a) a track capable of storing and feeding a plurality of substantially spherical beads by effect of gravity to a lower track end, (b) an enclosure sealingly housing said track, comprising:
a side wall enclosing outer lateral surfaces of said track,
a cover sealingly enclosing an upper track end of said track and upper end of said side wall, and
a base including upper and lower sections defining a plunger chamber, and a first bead chamber defined in said upper section communicating with said lower track end and said first bead chamber being offset along said plunger chamber relative to a bead exit opening in said lower section, (c) a plunger sealingly provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal horizontal bias force said plunger being capable of horizontal movement to align said second bead chamber with said exit opening, said normal biasing force of said biasing means capable of horizontally moving said plunger effective to reblock said exit opening upon removal of said opposing force, and wherein said plunger further comprises a notch receiving a fingered free end of said horizontal biasing means, said horizontal biasing means having an upper end attached to said track and a medial portion extending substantially perpendicularly relative to a longitudinal axis of the plunger to terminate in said free end.

* * * * *